United States Patent [19]

Noda et al.

[11] B 3,984,415

[45] Oct. 5, 1976

[54] 1-NITROPHENYLPYRIDO [2,3-D] PYRIMIDINE-2,4(1H,3H)-DIONES

[75] Inventors: Kanji Noda, Chikushino; Akira Nakagawa; Toshiharu Motomura, both of Tosu; Hiroyuki Ide, Fukuoka, all of Japan

[73] Assignee: Hisamitsu Pharmaceutical Co., Inc., Tosu, Japan

[22] Filed: Dec. 9, 1974

[21] Appl. No.: 531,096

[44] Published under the second Trial Voluntary Protest Program on February 10, 1976 as document No. B 531,096.

[30] Foreign Application Priority Data

Dec. 18, 1973 Japan............................. 48-142771

[52] U.S. Cl.................. 260/256.5 R; 260/256.4 F; 424/250; 424/251
[51] Int. Cl.²....................................... C07D 239/00
[58] Field of Search................ 260/256.5 R, 256.4 F

[56] References Cited
UNITED STATES PATENTS 3,235,554  2/1966  Papesch........................... 260/256.4

*Primary Examiner*—Leonard Schenkman
*Attorney, Agent, or Firm*—Browdy and Neimark

[57] ABSTRACT

The compounds of the present invention can be represented by the following formula:

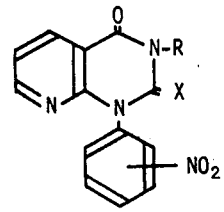

wherein R is selected from the group consisting of hydrogen, lower alkyl, substituted lower alkyl, unsaturated lower alkyl, substituted unsaturated lower alkyl and aralkyl; X is selected from the group consisting of O and S.

The compounds of the present invention possess a high degree of pharmacological activities such as anti-inflammatory, anti-ulcerative, analgetic, antipyretic, antihistaminic and central nervous system depressive activities, and certain of them are useful as new anti-inflammatory agents, analgesics and central nervous system depressants.

3 Claims, No Drawings

1-NITROPHENYLPYRIDO [2,3-d] PYRIMIDINE-2,4(1H,3H)-DIONES

DETAILED DESCRIPTION

The present invention relates to the compounds represented by the general formula I:

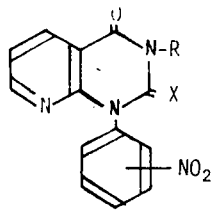

(I)

wherein R is selected from the group consisting of
1. hydrogen,
2. lower alkyl,
3. lower alkenyl,
4. lower alkynyl,
5. aralkyl,
6. lower alkyl substituted with the group consisting of halogen, hydroxyl, lower alkoxy, lower alkanoyloxy, vinyloxy, lower hydroxyalkoxy, lower cycloalkyl, carboxyl, lower alkoxycarbonyl, di(-lower alkyl)amino and six-membered cyclicamino;

X is selected from the group consisting of O and S.

All of the compounds of the present invention possess at least one of such pharmacological activities as anti-inflammatory, anti-ulcerative, analgetic, antipyretic, antihistaminic and central nervous system depressive activities as well as low toxicity, and most of them possess more than one of the said activities. It is to be noted, therefore, that certain of the compounds within the scope of the present invention are useful as new analgesics, anti-inflammatory agents and central nervous system depressants.

More particularly, the compounds of the present invention can be represented by the general formula II:

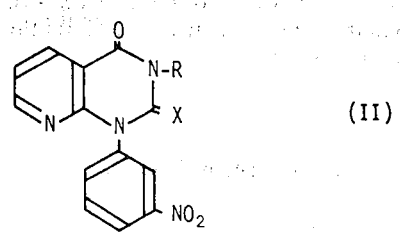

(II)

wherein R is selected from the group consisting of hydrogen, lower alkyl groups having from one to 6 carbon atoms, lower alkenyl groups having from 3 to 5 carbon atoms, haloallyl, propargyl, cyclopropylmethyl, lower haloalkyl groups having from one to 3 carbon atoms, lower trihaloalkyl groups having from one to 3 carbon atoms, acetoxyethyl, lower hydroxyalkyl groups having from 2 to 3 carbon atoms, lower alkoxyalkyl groups having from 2 to 4 carbon atoms, vinyloxyethyl, hydroxyethoxyethyl, carboxymethyl, ethoxycarbonylmethyl, 2,3-epoxypropyl, diethylaminoethyl, 4-methylpiperazinoethyl, benzyl, phenethyl and cinnamyl; X is selected from the group consisting of O and S.

The compounds of the present invention can be prepared in high yields by one of six basic routes as will be described hereinafter.

PREPARATION SERIES I

Reaction scheme [I]:

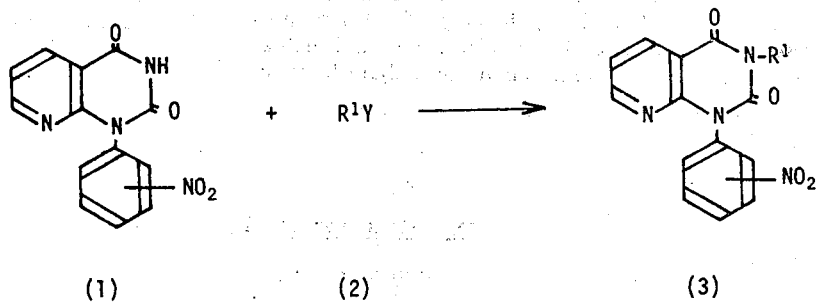

wherein $R^1$ is selected from the group consisting of lower alkyl, substituted lower alkyl, unsaturated lower alkyl and aralky; Y is selected from the group consisting of halogen, arylsulfonyloxy and inorganic acid ester rest. Examples of compounds of the general formula (2) include ethyl iodide, propargyl bromide, 2,2,2-trifluoroethyl p-toluenesulfonate, trimethyl phosphate and methyl fluorosulfate.

Reaction scheme [II]:

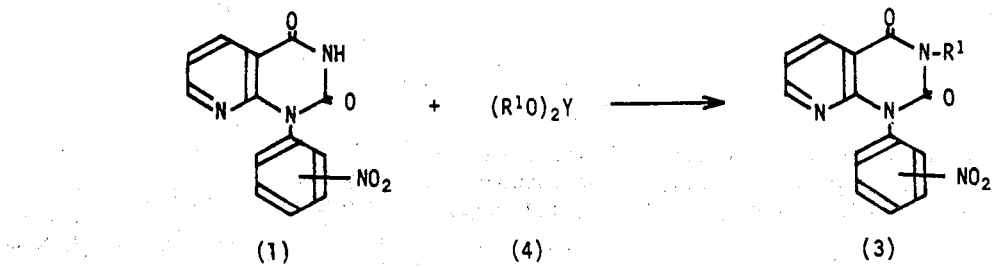

wherein R¹ has the same meanings as above; Y is selected from the group consisting of carbonyl (—CO—), sulfonyl (—SO₂—) and oxalyl (—CO—CO—). Examples of compounds of the general formula (4) include dimethyl sulfate, diethyl sulfate, diethyl carbonate and diethyl oxalate.

yield of the object product.

The desirable temperature is not critical but may be ambient or elevated temperature. Since the reaction proceeds very rapidly, room temperature is sufficient for the reaction and heating is not necessary. The period of reaction may range from 30 minutes to 3 hours, Reaction scheme [III] :

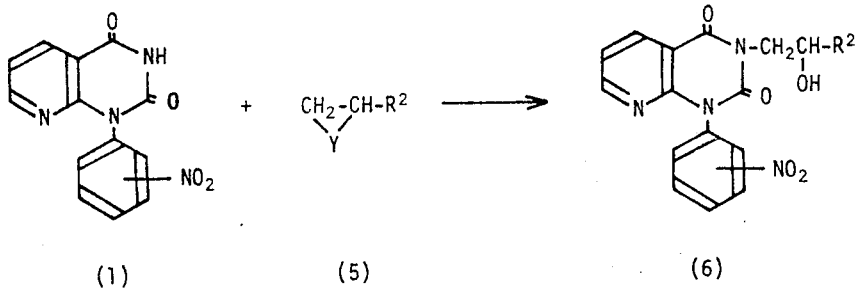

wherein $R^2$ is selected from the group consisting of hydrogen and lower alkyl; Y is selected from the group consisting of oxo (—O—), carbonyldioxo (—O—CO—O—) and sulfinyldioxo (—O—SO—O—). Examples of compounds of the general formula (5) include ethylene oxide, glycol sulfide, propylene oxide and ethylene carbonate.

The starting materials represented by the general formula (1) may be reacted with the said reagents of the general formulas (2), (4) and (5).

These reactions are preferably carried out in an organic solvent such as toluene, xylene, tetrahydrofuran, dioxane or dimethylformamide. The reactions as shown in the schemes [I] and [II] should preferably be processed in the presence of a metallic compound such as sodium alcoholate, sodium amide or sodium hydride, or an inroganic salt such as alkali hydroxide or carbonate. The employment of the said metallic compounds is particularly advantageous in order to obtain the highest and may be shortened by applying mild heating. On the other hand, when oxalic acid diesters and dialkyl carbonates are employed as N-alkylation agent in the reaction scheme [II], the reaction should preferably be performed in an autoclave at a temperature of 150°–240°C.

The reaction solvent is distilled off from the reaction mixture and the residue is mixed with water to precipitate the crystals of the desired product. Then the obtained crystals may be easily recrystallized from methanol or a similar solvent for purification.

In the reaction scheme [III], the reaction proceeds in a basic solvent at room temperature, but the reaction is finished in a short time when heated.

PREPARATION SERIES II

Preparation series II

Reaction scheme [IV] :

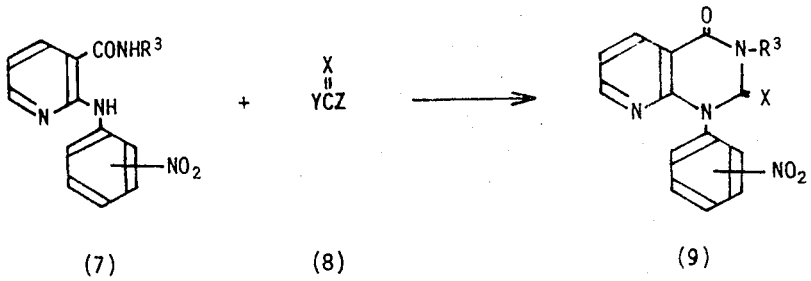

wherein $R^3$ is selected from the group consisting of hydrogen, lower alkyl, substituted lower alkyl and unsaturated lower alkyl; X is selected from the group consisting of O and S; Y and Z are the same or dissimilar and each may be halogen, lower alkoxy, trihalomethyl, amino or imidazolyl. Examples of compounds of the general formula (8) include urea, methylurea, diethylurea, N-propylurethane, trichloroacetyl chloride, N-ethoxycarbonylimidazole, 1,1'-carbonyldiimidazole, phosgene, ethyl chlorocarbonate, diethyl carbonate, 1,1'-thiocarbonyldiimidazole and thiophosgene.

Reaction scheme [V]:

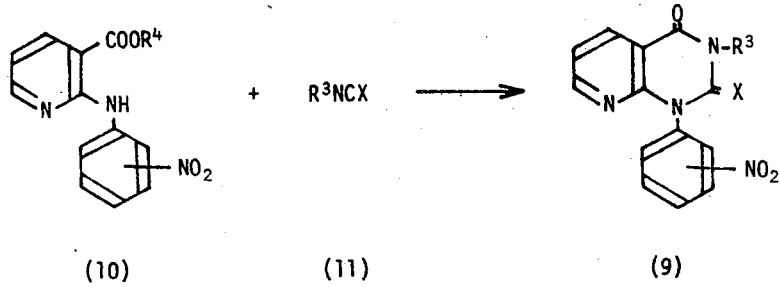

(10)    (11)    (9)

wherein $R^3$ and X have the same meanings as above; $R^4$ is lower alkyl. Examples of compounds of the general formula (11) include ethyl isocyanate, isopropyl isocyanate and methyl isothiocyanate.

The reactions of these schemes [IV] and [V] proceed smoothly under similar conditions preferably in an organic solvent such as dimethylformamide, diglyme, tetrahydrofuran or alcohol, but are most preferably performed in the presence of a metallic compound such as metallic sodium, sodium amide and sodium hydride, or an organic base such as trialkylamine and pyridine, or an inorganic base such as alkali hydroxide and carbonate. The first-mentioned metallic compounds are most effective to enhance the yield of product. The desirable temperature is not critical, and may be ambient or elevated temperature. However, the reactions are carried out under ice-cooling when phosgene or thiophosgene is used as a reagent. The reaction solvent is distilled off from the reaction mixture under reduced pressure and the residue obtained is mixed with water to precipitate a crude product. Recrystallization of this product from an organic solvent such as acetone or methanol yields pure crystals.

Reaction scheme [VI]:

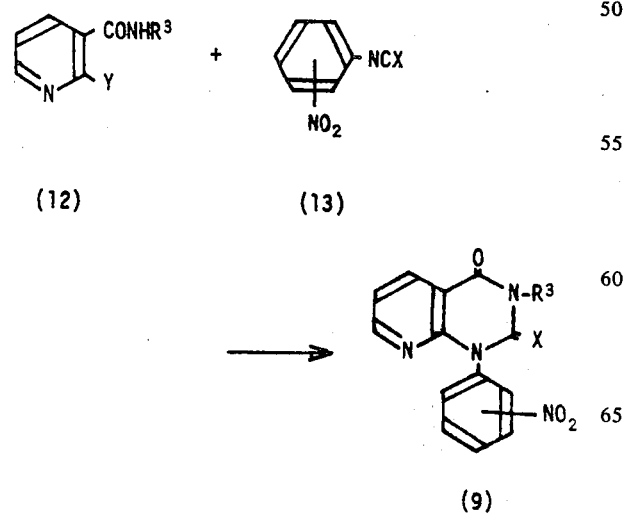

(12)    (13)

(9)

wherein Y is halogen; $R^3$ and X have the same meanings as above.

The reactions represented by the reaction scheme [VI] are preferably carried out in an organic solvent such as tetrahydrofuran, diglyme, dichloromethane, benzene, toluene, xylene or dimethylformamide. These reactions should be processed in the presence of a metallic compound such as sodium hydride, sodium amide or sodium alcoholate. The reaction temperature is not critical, but the reaction proceeds smoothly near or at the boiling point of the solvent used. The reaction product can be purified either by recrystallization from an organic solvent such as methanol, ethanol, ethyl acetate or acetone, or by column chromatography to yield pure crystals.

COMPOUNDS

The compounds of the present invention can be prepared by one of those routes as illustrated in the Reaction scheme I-VI. Some examples of these compounds and their melting points are shown in Table I.

Table I

Examples of the compounds obtained by the present invention

| Compound No. | X | R | Melting point (°C) |
|---|---|---|---|
| 1 | O | —H | 302 – 303 |
| 2 | " | —CH₃ | 234 – 235 |
| 3 | " | —C₂H₅ | 210 – 211 |
| 4 | " | —CH₂CH₂CH₃ | 184 – 185 |
| 5 | " | —CH(CH₃)₂ | 217 – 218 |
| 6 | " | —CH₂CH₂CH₂CH₃ | 146 – 147 |
| 7 | " | —CH₂CH(CH₃)₂ | 199 – 200 |
| 8 | " | —CH₂CH₂CH₂CH₂CH₃ | 150 – 151 |
| 9 | " | —CH₂CH=CH₂ | 192 – 193 |
| 10 | " | —CH₂CH=C(CH₃)₂ | 178 – 179 |
| 11 | " | —CH₂CH=CHCl | 217 – 218 |
| 12 | " | —CH₂C≡CH | 239 – 240 |
| 13 | " | —CH₂-cyclopropyl | 165 – 166 |
| 14 | " | —CH₂CH₂Cl | 202 – 203 |
| 15 | " | —CH₂CH₂F | 233 – 234 |
| 16 | " | —CH₂CF₃ | 228 – 229 |
| 17 | " | —CH₂CH₂CH₂Cl | 159 – 160 |

Table I-continued

Examples of the compounds obtained by the present invention

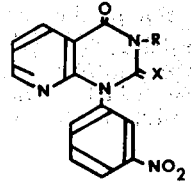

| Compound No. | X | R | Melting point (°C) |
|---|---|---|---|
| 18 | O | —CH$_2$CH$_2$OH | 212 – 213 |
| 19 | " | —CH$_2$CH$_2$CH$_2$OH | 173 – 174 |
| 20 | " | —CH$_2$CH—CH$_2$ (epoxide) | 201 – 202 |
| 21 | " | —CH$_2$CH$_2$OCOCH$_3$ | 195 – 196 |
| 22 | " | —CH$_2$OCH$_3$ | 184 – 186 |
| 23 | " | —CH$_2$CH$_2$OC$_2$H$_5$ | 163 – 164 |
| 24 | " | —CH$_2$CH$_2$OCH=CH$_2$ | 182 – 183 |
| 25 | " | —CH$_2$CH$_2$OCH$_2$CH$_2$OH | 176 – 178 |
| 26 | " | —CH$_2$COOH | 244 – 245 |
| 27 | " | —CH$_2$COOC$_2$H$_5$ | 200 – 201 |
| 28 | " | —CH$_2$CH$_2$—N(C$_2$H$_5$)$_2$ | 156 – 158 (Hydrochloride) |
| 29 | " | —CH$_2$CH$_2$—N(piperazinyl)N-CH$_3$ | 250 – 253 (Hydrochloride) |
| 30 | " | —CH$_2$—(cyclohexyl) | 219 – 220 |
| 31 | " | —CH$_2$CH$_2$—(phenyl) | 227 – 228 |
| 32 | " | —CH$_2$CH=CH—(phenyl) | 191 – 192 |
| 33 | S | —CH$_3$ | 265 – 266 |
| 34 | " | —C$_2$H$_5$ | 239 – 240 |
| 35 | " | —CH$_2$CH$_2$CH$_3$ | 190 – 191 |
| 36 | " | —CH$_2$CH=CH$_2$ | 248 – 250 |
| 37 | " | —CH$_2$C≡CH | 209 – 210 |
| 38 | " | —CH$_2$—(cyclopropyl) | 199 – 200 |
| 39 | " | —CH$_2$CF$_3$ | 242 – 243 |
| 40 | " | —CH$_2$—(phenyl) | 224 – 226 |

PHARMACOLOGICAL ACTIVITIES

With respect to numerous compounds of the present invention, the acute toxicity was tested to ensure their safety, and further central nervous system depressive, anti-inflammatory and analgetic effects were tested to prove their excellent activities. The results of each test are indicated in Table II. Each test was conducted in the following manner.

1. Acute toxicity

Each test compound suspended in 0.5% tragacanth-saline solution was administered intraperitoneally or orally to dd-strain male mice (16–24 g). The lethal dose was estimated from the death of animals 72 hours after administration.

2. Anti-inflammatory effect

A group of five Wistar-strain male rats (100–150 g) were orally administered with each test compound suspended in 0.5% tragacanth-saline solution. After 30 minutes 0.5%–1.0% carrageenin suspended in the water for injection was injected subcutaneously to a hind paw. After 3 hours the carrageenin edema was measured by volume and the inhibition percentage was determined with respect to the results for the control animals. The inhibition percentages were shown with the notations as follows:

less than 15 % : ±    31–45 % : ++    more than 61 % : ++++
16–30 % : +           46–60 % : +++

3. Analgetic effect

Each test compound suspended in 0.5% tragacanth-saline solution was orally administered to dd-strain male mice (18–20 g). After one hour 0.6% acetic acid solution was intraperitoneally injected in a volume of 0.1 ml/10 g. The writhing syndrome was observed for 10 minutes from 30 minutes after the injection, and 50% analgetic effective dose (ED$_{50}$) and its 95% confidential limits were calculated by Litchfield-Wilcoxon's method.

4. Central nervous system depressive effect

Each test compound suspended in 0.5% tragacanth-saline solution was injected intraperitoneally to dd-strain male mice (16–24 g). The disappearance of righting reflex was observed under noiseless circumstances. The dose required for the disappearance of righting reflex is indicated with the following notations:

more than 1,000 (mg/kg)) : −    100–30 (mg/kg) : ++
1,000–300 (mg/kg) : ±           30–10 (mg/kg) : +++
300–100 (mg/kg) : +             less than 10 (mg/kg) : ++++

Table II

Anti-inflammatory, Analgetic and Central Nervous System Depressive Effects, and Acute Toxicity of the Object Compounds of General Formula:

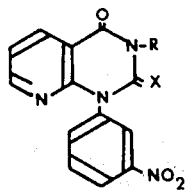

| Standard compounds | anti-inflammatory effect dose(mg/kg) | analgetic effect ED$_{50}$ (95%C.L.) (mg/kg) | CNS depressive effect | acute toxicity (mg/kg) i.p. |
|---|---|---|---|---|
| phenylbutazone | 50 ++ | 10  290 (113–435) 180 | ± | 300–1000 |

Table II-continued

Anti-inflammatory, Analgetic and Central Nervous System Depressive Effects, and Acute Toxicity of the Object Compounds of General Formula:

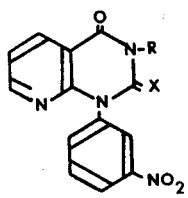

| Standard compounds | anti-inflammatory effect dose(mg/kg) | | analgetic effect ED$_{50}$ (95%C.L.) (mg/kg) | CNS depressive effect | acute toxicity (mg/kg) |
|---|---|---|---|---|---|
| | 50 | 10 | | | i.p. |
| flufenamic acid | + | ± | (131–245) i.p. 56.0 | – | 300–1000 |
| aminopyrine | ± | ± | (43.0–73.0) | / | 100–300 |
| methaqualone | / | / | / | +++ | 300–1000 |
| diazepam | + | ± | / | ++ | 300–1000 |

Known analogous compounds

| | | anti-inflammatory effect dose(mg/kg) | | analgetic effect ED$_{50}$ (95%C.L.) (mg/kg) | CNS depressive effect | acute toxicity (mg/kg) | |
|---|---|---|---|---|---|---|---|

| R$^1$ | R$^2$ | 100 | 50 | 20 | 10 | | | i.p. | p.o. |
|---|---|---|---|---|---|---|---|---|---|
| phenyl-CF$_3$ | —C$_2$H$_5$ | ++++ | ++++ | +++ | +++ | 10.0 (2.0–51.4) | +++ | 600 | 665 |
| phenyl-Cl | —CH$_3$ | +++ | +++ | +++ | ++ | 7.1 (2.7–18.5) | ± | >1000 | >1000 |
| phenyl-Br | —CH$_2$CH$_2$CH$_3$ | ++++ | +++ | ++ | +++ | 20.0 (2.9–137.0) | ± | >1000 | / |

Object compounds

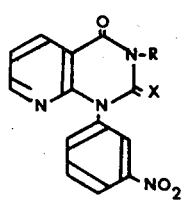

| | anti-inflammatory effect dose(mg/kg) | analgetic effect ED$_{50}$ (95%C.L.) (mg/kg) | CNS depressive effect | acute toxicity (mg/kg) |
|---|---|---|---|---|

| X | R | 100 | 50 | 20 | 10 | | | i.p. | p.o. |
|---|---|---|---|---|---|---|---|---|---|
| O | —CH$_3$ | ++++ | ++++ | +++ | +++ | 0.175 (0.07–0.42) | + | 200–300 | 1000–2000 |
| " | —C$_2$H$_5$ | / | ++++ | ++++ | ++++ | 0.113 (0.027–0.476) | + | 300–1000 | 1000–2000 |
| " | —CH$_2$CH$_2$CH$_3$ | +++ | ++ | +++ | +++ | 2.6 (1.05–6.40) | – | 1000 | >2000 |
| " | —CH(CH$_3$)$_2$ | ++++ | +++ | +++ | +++ | 2.15 (0.93–4.97) | ++ | >1000 | / |
| " | —CH$_2$CH(CH$_3$)$_2$ | ++ | ++ | ++ | / | 3.1 (1.20–8.30) | ± | 1000 | >2000 |
| " | —CH$_2$-cyclopropyl | ++++ | ++++ | ++++ | ++++ | 0.12 (0.048–0.298) | ++++ | 300 | 200–500 |
| " | —CH$_2$CH=CH$_2$ | ++++ | ++++ | +++ | ++++ | 2.6 (1.05–6.40) | ++ | 300–1000 | >2000 |
| " | —CH$_2$CH=C(CH$_3$)$_2$ | +++ | ++++ | ++ | ++ | 0.43 (0.18–1.02) | – | 200–500 | >2000 |
| " | —CH$_2$C≡CH | ++++ | +++ | +++ | +++ | 1.15 (0.43–3.09) | ± | >1000 | >2000 |

Table II-continued

| Object compounds | anti-inflammatory effect dose(mg/kg) | | | | analgetic effect $ED_{50}$ (95%C.L.) (mg/kg) | CNS depressive effect | acute toxicity (mg/kg) | |
|---|---|---|---|---|---|---|---|---|
| | 100 | 50 | 20 | 10 | | | i.p. | p.o. |

| X | R | 100 | 50 | 20 | 10 | | | i.p. | p.o. |
|---|---|---|---|---|---|---|---|---|---|
| O | —CH$_2$CH$_2$Cl | ++++ | +++ | ++++ | +++ | 0.19 (0.09–0.41) | — | >1000 100– | >2000 |
| " | —CH$_2$CH$_2$F | +++ | ++++ | +++ | ++++ | ≈0.01 1.28 | ++ | 300 | 2000 |
| " | —CH$_2$CF$_3$ | +++ | +++ | ++++ | +++ | (0.53–3.10) 0.42 | + | >1000 | >2000 |
| " | —CH$_2$CH$_2$OH | ++ | ++ | / | / | (0.15–1.15) | ± | >1000 | >2000 |
| " | —CH$_2$CH$_2$CH$_2$OH | +++ | +++ | +++ | ++ | ≈ 1.0 0.16 | ± | >1000 | >2000 |
| " | —CH$_2$CH$_2$OCOCH$_3$ | ++ | + | / | / | (0.06–0.43) 0.168 | — | >1000 | 2000 |
| | —CH$_2$CH$_2$OC$_2$H$_5$ | ++ | +++ | +++ | ++ | (0.06–0.44) 33.0 | ++ | >1000 | / |
| " | —CH$_2$COOH | / | ++ | + | / | (13.5–80.9) 45.0 | + | >1000 | >2000 |
| " | —CH$_2$COOC$_2$H$_5$ | +++ | +++ | ++ | ++ | (17.3–117) 1.7 | ± | 1000 | >2000 |
| " | —Ch$_2$-⌬ | ++++ | +++ | +++ | ++ | (0.63–4.56) | — | 1000 | 2000 |
| " | —CH$_2$CH$_2$-⌬ | ± | — | — | / | >100 | + | >1000 | >2000 |
| " | —CH$_2$CO-⌬-Cl | ± | / | / | / | >100 | — | >1000 | >2000 |
| S | —CH$_3$ | / | +++ | / | +++ | (0.23–1.55) | — | >1000 | >2000 |
| " | —C$_2$H$_5$ | / | +++ | / | +++ | ≈ 0.2 | ++ | >1000 | >2000 |
| " | —CH$_2$CH$_2$CH$_3$ | / | + | / | + | ≈ 1000 0.23 | — | >1000 | >2000 |
| " | —CH$_2$CF$_3$ | / | +++ | / | ++++ | (0.07–0.77)/ ± | >1000 | >2000 | |

The present invention is illustrated hereinafter, but not limited to these Examples.

EXAMPLE 1

2.8 g of 1-(m-nitrophenyl)pyrido[2,3-d]pyrimidine-2,4(1H,3H)-dione was dissolved in 30 ml of dry dimethylformamide. To the solution was added 0.6 g of approximately 50% sodium hydride and stirring was performed for 30 minutes. To this was added 3.4 g of allyl iodide and the mixture was reacted for 3 hours at room temperature. Then the solvent was evaporated from the mixture under reduced pressure. To the residue obtained was added water to precipitate a crude product. Recrystallization of this product from methanol gave 2.3 g of 1-(m-nitrophenyl)-3-allylpyrido[2,3-d]pyrimidine-2,4(1H,3H)-dione as pale yellow prisms, melting at 188–189°C.

Analysis—Calculated for C$_{16}$H$_{12}$N$_4$O$_4$: C, 59.26; H, 3.73; N, 17.28. Found: C, 59.12; H, 3.87; N, 17.31.

EXAMPLE 2

To a solution of 1-(m-nitrophenyl)pyrido[2,3-d]pyrimidine-2,4(1H,3H)-dione and 30 ml of dry dimethlformamide was dimethylformamide 0.6 g of about 50% sodium hydride, and stirring was performed for 30 minutes. To this was added dropwise 2.3 g of methyl fluorosulfate and the mixture was reacted for one hour at room temperature. Then the mixture was neutralized with 5 % sodium carbonate solution and concentrated under reduced pressure to leave a residue, to which was added water to yield a crude product. This products was recrystallized from acetone to give 2.6 g of 1-(m-nitrophenyl)-3-methylpyrido[2,3-d]pyrimidine-2,4(1H,3H)-dione as pale yellow prisms, melting at 234°–235°C.

Analysis—Calculated for C$_{14}$H$_{10}$ O$_4$N$_4$: C, 59.63; H, 3.13N, 17.39. Found: C, 59.52; H, 3.21; N, 17.21.

EXAMPLE 3

2.8 g of 1-(m-nitrophenyl)pyrido[2,3-d]pyrimidine-2,4(1H,3H)-dione was dissolved in 30 ml of dry dimethylformamide. To this was added 4.2 g of trimethyl phosphate and the mixture was refluxed for 6 hours. After the reaction was complete, the solvent was distilled off from the mixture, and to the residue obtained was added water to precipitate a crude product. The product was recrystallized from acetone to yield 2.5 g of 1-(m-nitrophenyl)-3-methylpyrido[2,3-d]pyrimidine-2,4(1H,3H)-dione as pale yellow prisms, melting at 234°–235°C.

EXAMPLE 4

To a mixture of 2.8 g of 1-(m-nitrophenyl)-pyrido[2,3-d]pyrimidine-2,4 (1H,3H)-dione and 30 ml of dry dimethylformamide was added 0.6 g of approximately 50 % sodium hydride. The mixture was stirred for 30 minutes at room temperature and for additional 10 minutes at a temperature of 70°–80°C. To the mixture was further added dropwise 3.4 g of benzyl bromide and stirring was continued for 30 minutes. The solvent was removed from the resulting mixture by distillation, and to the residue was added water to give a crude precipitate. This product was recrystallized from a mixture of methanol and dimethylformamide to yield 3.3 g of 1-(m-nitrophenyl)-3-benzylpyrido[2,3-d]pyrimidine-2,4(1H,3H)-dione as pale yellow prisms, melting at 219°–220°C.

Analysis—Calculated for $C_{20}H_{14}N_4O_4$ : C, 64.17; H, 3,77; N, 14.97. Found: C, 64.03; H, 3.84; N, 14.82.

EXAMPLE 5

2.8 g of 1-(m-nitrophenyl)pyrido[2,3-d]pyrimidine-2,4(1H,3H)-dione was dissolved in 30 ml of dry dimethylformamide. To the solution was added 0.6 g of about 50 % sodium hydride, and stirring was performed for 30 minutes. To the mixture was further added 3.5 g of diethylsulfite and the whole was reacted for 2 hours at room temperature. After the reaction was finished, the solvent was distilled off from the mixture under reduced pressure. To the residue thus obtained was added water to precipitate a crude product. This product was recrystallized from methanol to yield 2.7 g of 1-(m-nitrophenyl)-3-ethylpyrido[2,3-d]pyrimidine-2,4(1H,3H)-dione as pale yellow prisms, melting at 210°–211°C.

Analysis—Calculated for $C_{15}H_{12}N_4O_4$ : C, 57.69; H, 3.87; N, 17.94. Found: C, 57.52 H, 3,81; N, 17.93.

EXAMPLE 6

2.8 g of 1-(m-nitrophenyl)pyrido[2,3-d]pyrimidine-2,4(1H,3H)-dione was dissolved in 30 ml of dimethylformamide. To the solution was added 0.6 g of about 50 % sodium hydride and the whole was stirred for 20 minutes at room temperature, and then heated up to 90°C. To this was added dropwise a solution of 7.5 g of 2,2,2-trifluoroethyl p-toluenesulfonate and 20 ml of tetrahydrofuran and the mixture was reacted for 2 hours. After the reaction was complete, the solvent was removed from the resulting mixture by distillation, and to the residue obtained was added water to precipitate a crude product. This product was recrystallized from methanol to yield 3.2 g of 1-(m-nitrophenyl)-3-(2,2,2-trifluoroethyl)pyrido[2,3-d]pyrimidine-2,4(1H,3H)-dione as pale yellow prisms, melting at 228–229°C.

Analysis—Calculated for $C_{14}H_9F_3N_4O_4$ : C, 49.19; H, 2.48; N, 15.30, Found: C, 49.00; H, 2.49; N, 15.21.

EXAMPLE 7

To a solution of 2.8 g of 1-(m-nitrophenyl)-pyrido[2,3-d]pyrimidine-2,4 (1H,3H)-dione and 30 ml of dimethylformamide was added 0.53 g of 55 % sodium hydride, and the solution was heated up to 150°C. To this was added 0.97 g of ethylene carbonate, and the mixture was reacted for one hour at 150°C. After the reaction was complete, the solvent was distilled off from the resulting mixture under reduced pressure. To the residue obtained was added water to precipitate a crude product. This product was recrystallized from methanol to yield 2.8 g of 1-(m-nitrophenyl)-3-(2-hydroxyethyl)pyrido[2,3-d] pyrimidine-2,4(1H,3H)-dione as pale yellow prisms, melting at 212°–213°C.

Analysis—Calculated for $C_{15}H_{12}N_4O_5$ : C, 54.88; H, 3.68; N, 17.07. Found: C, 54.93; ; H, 3.65; N, 17.16.

EXAMPLE 8

To a solution of 3.0 g of 2-(m-nitroanilino)niotinic acid allylamide and 25 ml of dry tetrahydrofuran was added 1.0 g of approximately 55 % sodium hydride, and the whole was stirred for 30 minutes. To this was added dropwise 4.2 g of 1-ethoxycarbonylimidazole, and the mixture was refluxed for 3 hours. After the reaction was complete, the solvent was distilled off from the reaction mixture to leave a residue, to which was added water to precipitate a crude product. This product was recrystallized from methanol to yield 3.0 g of 1-(m-nitrophenyl)-3-allylpyrido[2,3-d] pyrimidine-2,4(1H,3H)-dione as pale yellow prisms, melting at 188°–189°C.

Analysis-Calculated for $C_{16}H_{12}N_4O_4$ : C, 59.26; H, 3.73; N, 17.28. Found: C, 59.03; H, 3.82; N, 17.43.

EXAMPLE 9

To a solution of 1.25 g of 2-(m-nitroanilino)nicotinic acid methylamide and 20 ml of tetrahydrofuran was added 0.48 g of approximately 50 % sodium hydride and the mixture was stirred for 30 minutes. To the mixture was further added dropwise 2.3 g of thiophosgene under cooling with ice and the resultant mixture was allowed to stand for 30 minutes at room temperature. An excess of thiophosgene was decomposed with adding methanol-ammonia solution. The solvent was distilled off from the mixture to give a residue, to which was added water to precipitate a crude product. Recrystallization of this product from acetone gave 1.2 g of 1-(m-nitrophenyl)-3-methyl-2-thio-4-oxo-1,2,3,4-tetrahydropyrido[2,3-d]pyrimidine as pale yellow prisms, melting at 265°–266°C.

Analysis—Calculated for $C_{14}H_{10}N_4O_3S$ : C, 53.51; H, 3.21; N, 17.83. Found: C, 53.63; H, 3.19; N, 17.69.

EXAMPLE 10

To a solution of 1.9 g of 2-chloronicotinic acid propargylamide and 20 ml of dry dimethylformamide was added 1.0 g of 50 % sodium hydride, and the solution was stirred for 30 minutes. To this was further added 2.3 g of m-nitrophenylisothiocyanate and the mixture was refluxed for 6 hours. After the reaction was complete, the mixture was concentrated under reduced pressure to removed the solvent. The concentrate was passed through a column of silica gel and the adsorbate was eluted with ethyl acetate. The crystals thus obtained were further purified by recrystallization from methanol to yield 2.3 g of 1-(m-nitrophenyl)-3-propargyl-2-thio-4-oxo-1,2,3,4-tetrahydropyrido[2,3-d]pyrimidine as pale yellow prisms, melting at 209°–210°C.

Analysis—Calculated for $C_{16}H_{10}N_4O_3S$ : C, 55.80; H, 4.68; N, 16.27. Found: C, 55.77; H, 4.65; N, 16.31.

EXAMPLE 11

To a solution of 5.7 g of 2-(m-nitroanilino)nicotinic acid ethyl ester and 50 ml of dry tetrahydrofuran was added 1.1 g of sodium amide and the solution was stirred for one hour. To this was added dropwise under cooling 2.9 g of ethyl isocyanate and this mixture was reacted at 60°C for 10 hours. After the reaction was complete, the solvent was distilled off from the mixture, and to the residue obtained was added water to precipitate a crude product. This product was collected by filtration and recrystallized from methanol to give 3.4 g of 1-(m-nitrophenyl)-3-ethylpyrido[2,3-d]pyrimidine-2,4(1H,3H)-dione as colorless needles, melting at 210°–211°C.

What is claimed is:

1. A compound of the formula:

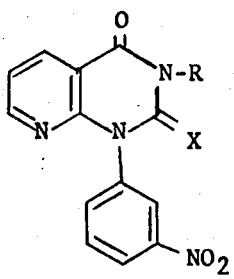

wherein R is selected from the group consisting of hydrogen, lower alkyl having from one to 6 carbon atoms, lower alkenyl having from 3 to 5 carbon atoms, propargyl, cyclopropylmethyl, lower haloalkyl having from one to 3 carbon atoms, lower trihaloalkyl having from one to 3 carbon atoms, vinyloxyethyl, acetoxyethyl, lower hydroxyalkyl having from 2 to 3 carbon atoms, lower alkoxyalkyl having from 2 to 4 carbon atoms, haloallyl, hydroxyethoxyethyl, ethoxycarbonylmethyl, carboxymethyl, 2,3-epoxypropyl, diethylaminoethyl, 4-methylpiperazinoethyl, benzyl, phenethyl and cinnamyl; x is selected from the group consisting of O and S.

2. A compounnd in accordance with claim 1 of the formula:

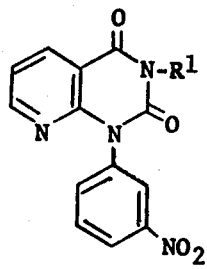

wherein $R^1$ is selected from the group consisting of hydrogen, lower alkyl having from one to 6 carbon atoms, lower alkenyl having from 3 to 5 carbon atoms, propargyl, cyclopropylmethyl, lower haloalkyl groups having from one to 3 carbon atoms, lower trihaloalkyl having from one to 3 carbon atoms, vinyloxyethyl, acetoxyethyl, lower hydroxyalkyl having from 2 to 3 carbon atoms, lower alkoxyalkyl having from 2 to 4 carbon atoms, haloallyl, hydroxyethoxyethyl, ethoxycarbonylmethyl, carboxymethyl, 2,3-epoxypropyl, diethylaminoethyl, 4-methylpiperazinoethyl, benzyl, phenethyl and cinnamyl.

3. A compound in accordance with claim 1 of the formula:

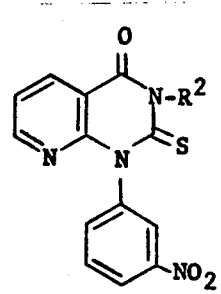

wherein $R^2$ is selected from the group consisting of lower alkyl having from one to 6 carbon atoms, allyl, propargyl, cyclopropylmethyl, 2,2,2-trifluoroethyl and benzyl.

* * * * *